(12) United States Patent
Paulus

(10) Patent No.: US 11,464,995 B2
(45) Date of Patent: Oct. 11, 2022

(54) MAGNETIC NERVE STIMULATOR

(71) Applicant: Kenneth Paulus, Charlotte, NC (US)

(72) Inventor: Kenneth Paulus, Charlotte, NC (US)

(*) Notice: Subject to any disclaimer, the term of this patent is extended or adjusted under 35 U.S.C. 154(b) by 0 days.

(21) Appl. No.: 17/111,833

(22) Filed: Dec. 4, 2020

(65) Prior Publication Data

US 2021/0170188 A1    Jun. 10, 2021

Related U.S. Application Data

(60) Provisional application No. 62/943,660, filed on Dec. 4, 2019.

(51) Int. Cl.
*A61N 2/02* (2006.01)
*A61N 2/00* (2006.01)

(52) U.S. Cl.
CPC .............. *A61N 2/02* (2013.01); *A61N 2/006* (2013.01)

(58) Field of Classification Search
CPC ................................. A61N 2/006; A61N 2/02
See application file for complete search history.

(56) References Cited

U.S. PATENT DOCUMENTS

| | | |
|---|---|---|
| 5,453,073 A | 9/1995 | Markoll |
| 5,984,854 A | 11/1999 | Ishikawa et al. |
| 2014/0330067 A1 | 11/2014 | Jordan |
| 2015/0157873 A1 | 6/2015 | Sokolowski |
| 2017/0291037 A1 | 10/2017 | Tamiya et al. |
| 2018/0104484 A1 | 4/2018 | Ryaby et al. |

FOREIGN PATENT DOCUMENTS

| EP | 3479872 | 5/2019 |
|---|---|---|
| WO | 1991015263 | 10/1991 |

*Primary Examiner* — Christine H Matthews
(74) *Attorney, Agent, or Firm* — Blake E. Vande Garde; Avek IP, LLC

(57) ABSTRACT

An apparatus for muscle stimulation comprising a platform with an upper surface and a lower surface, a pair of cross rails mounted under the lower surface of the platform, a sled slidably mounted to the cross rails, a pair of sled rails mounted to the sled, a bracket slidably mounted to the sled rails, a handle secured to the bracket, wherein the handle allows an operator to adjust the location of the bracket to any location desired under the platform, a magnetic nerve/muscle stimulator mounted to the bracket which includes one or more magnets and one or more electrical coils and a control panel operationally associated with the magnetic nerve/muscle stimulator, the control panel controlling the power supplied to the magnetic nerve/muscle stimulator, wherein the magnetic never/muscle stimulator generates and directs a magnetic field into the anatomy of a patient positioned on the upper surface of the platform.

13 Claims, 12 Drawing Sheets

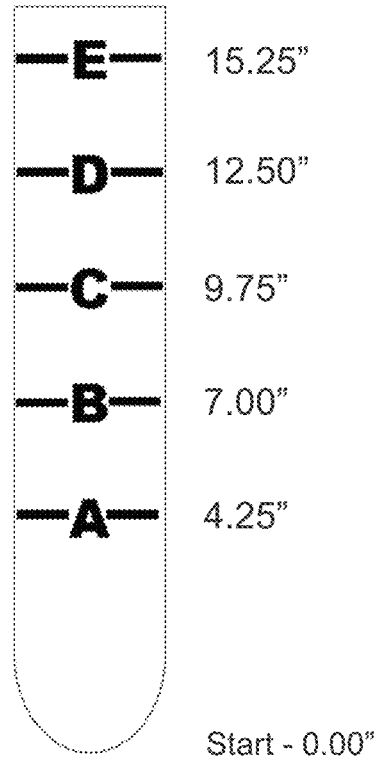

- Letters are centered to the handle
- Line notches center to the letter and on left and right side to edge of handle.
- Both Letters and Lines help the user align the magnet to the appropriate location
- Measurements start from the curved end of the handle

FIG. 17

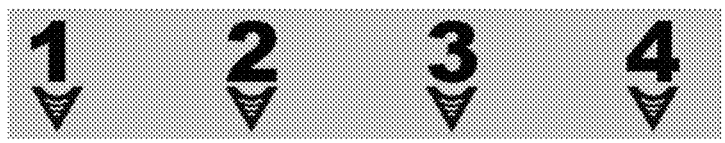

- Font is Arial Black
- Arrow is the REACT logo "A" turned upside down
- Number line is 1 - 36
- Space between Arrows is 1.5 inches
- Number Font Size is TBD
- Strip is REACT Green with printed Black on top
- Strip is TBD x TBD

FIG. 18

MAGNETIC NERVE STIMULATOR

CROSS REFERENCE TO RELATED APPLICATION

This application claims the priority of the provisional application Ser. No. 62/943,660 filed Dec. 4, 2019. Applicant hereby incorporates by reference the entire content of provisional application Ser. No. 62/943,660.

FIELD OF INVENTION

This invention pertains to the activation of nerves by topical stimulators to control or influence muscles, tissues, blood flow, organs, neuromuscular disorders or sensation, including pain, in humans and mammals.

BACKGROUND OF THE INVENTION

A nerve cell can be excited many different ways. A direct method is to increase the electrical charge within the nerve, thereby increasing the membrane potential inside the nerve with respect to the surrounding extracellular fluid. Devices that fall under the umbrella of Functional Electrical Stimulation (FES) achieves the excitation of the nerves by directly stimulating the nerves via electrodes which are either placed on a patient's skin or in vivo next to the targeted nerve group. The electric fields necessary for the charge transfer are generated via the wires of the electrodes.

FES is accomplished through a mechanism which involves a half-cell reaction. Electrons flow in wires and ions flow in the body. At the electro-electrolytic interface, a half-cell reaction occurs to achieve the electron-ion interchange. Unless this half-cell reaction is maintained in the reversible regime, necrosis will result—partially because of the oxidation of the half-cell reaction and partially because of the chemical imbalance accompanied by it.

The advantage of FES is that the stimulation is accomplished from extremely small electrodes with very low current and voltage levels. The disadvantage is that it involves the above described half-cell reactions. Most rehabilitation regimen using FES place the electrodes directly on the skin. A conductive gel or buffering solution is used between the electrodes and the skin surface. Long term excitation of nerve or muscle tissue is generally accompanied by skin irritation due to the current concentration at the electrode/skin interface. This problem is aggravated when larger excitation levels are required for more comprehensive stimulation or recruitment of the nerve group.

Magnetic stimulation realizes the electric fields necessary for the charge transfer by induction without the disadvantages of FES. Rapidly changing magnetic fields induce electric fields in the biological tissue. When properly oriented, and when the proper magnitude is achieved, the magnetically induced electric field achieves the transfer of charge directly into the nerve to be excited. When the localized membrane potential inside the nerve rises with respect to its normal negative ambient level of approximately −90 millivolts (this level being sensitive to the type of nerve and local pH of the surrounding tissue), the nerve "fires", sending a signal to the motor cortex of the brain which in turn sends a protein response back to the targeted muscle group to contract. This mechanism creates a true neuromuscular response between the muscle and brain.

The present invention is specifically designed for non-invasive external stimulation of selected nerve or nerve groups. Magnetic excitation has the attractive feature of not requiring electrode skin contact. Thus, stimulation can be achieved through clothing, bandages and even immobilizing splints or casts. This overcomes the problem of inconvenience and preserves a patient's modesty. Secondly, because there is no direct contact, stronger excitation levels can be realized without additional skin irritation. The present invention provides the ability to achieve higher levels of focusing of the magnetic field and thus stimulation within the patient. Commensurate with this greater level of focusing comes some flexibility in the number of possible applications that might be targeted. Also accompanying the focusing is a higher level of power efficiency.

Thus, there is clearly a need for a treatment and system for the activation of nerves by topical stimulators to control or influence muscles, tissues, organs, or sensation, including pain, in humans and mammals.

SUMMARY OF THE INVENTION

An apparatus for muscle stimulation comprising a platform with an upper surface and a lower surface, a pair of cross rails mounted under the lower surface of the platform, a sled slidably mounted to the cross rails, a pair of sled rails mounted to the sled, a bracket slidably mounted to the sled rails, a handle secured to the bracket, wherein the handle allows an operator to adjust the location of the bracket to any location desired under the platform, a magnetic nerve/muscle stimulator mounted to the bracket which includes one or more magnets and one or more electrical coils and a control panel operationally associated with the magnetic nerve/muscle stimulator, the control panel controlling the power supplied to the magnetic nerve/muscle stimulator, wherein the magnetic never/muscle stimulator generates and directs a magnetic field into the anatomy of a patient positioned on the upper surface of the platform.

DESCRIPTION OF THE DRAWINGS

For the purpose of illustrating the invention, there is shown in the drawings a form that is presently preferred; it being understood, however, that this invention is not limited to the precise arrangements and instrumentalities shown.

FIG. 17 is an embodiment of a letter diagram on the handle of the instant invention.

FIG. 18 is an embodiment of a number diagram on the table of the instant invention.

DETAILED DESCRIPTION

Figure 1:
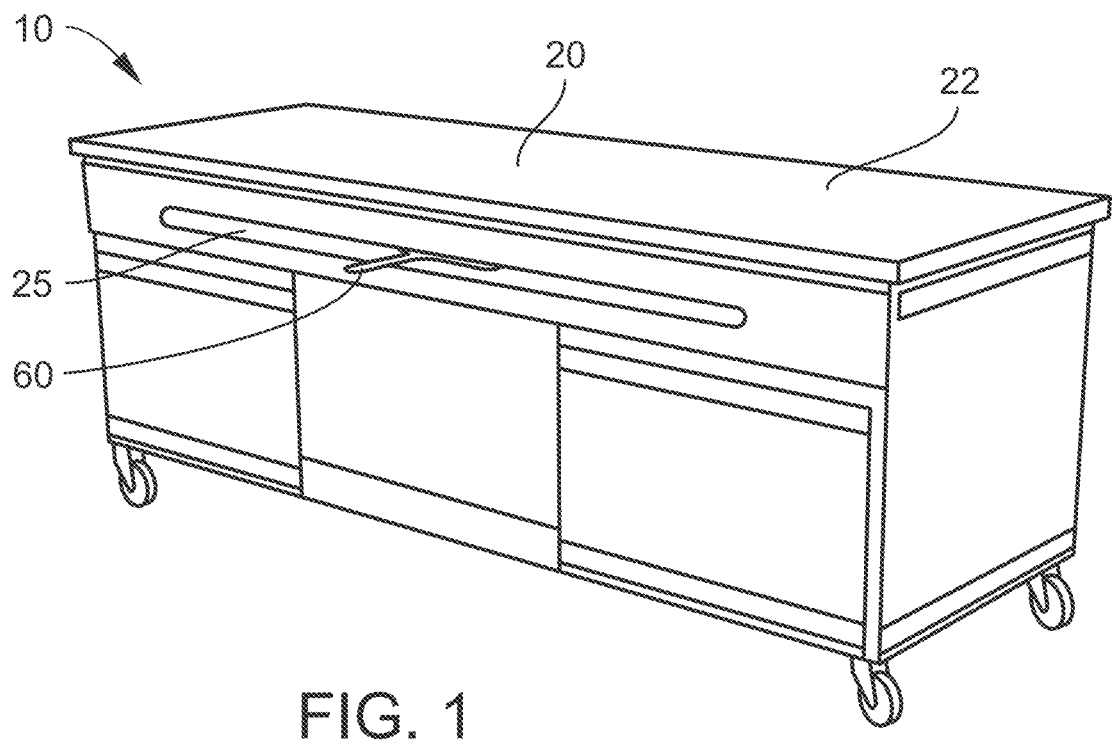
FIG. 1 is a side proximal view of one embodiment of a table used in the instant invention.
Figure 2:
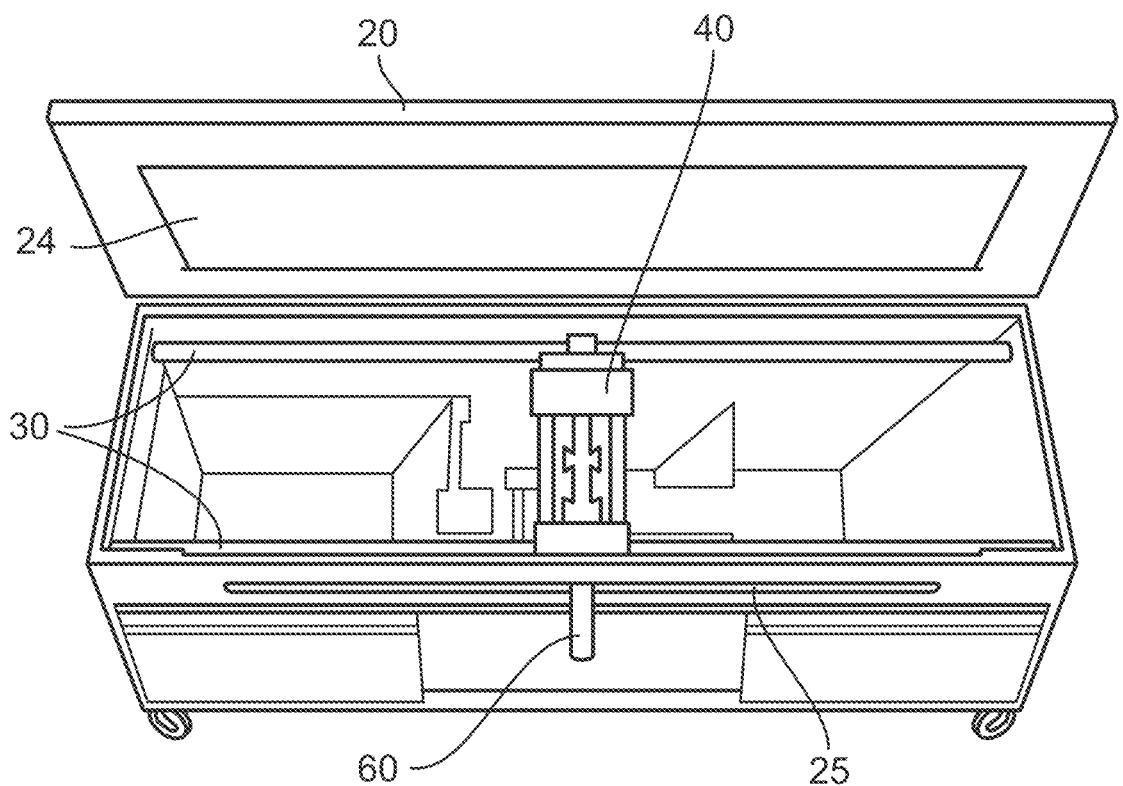
FIG. 2 is a downward proximal view of one embodiment of a table used in the instant invention.
Figure 3:
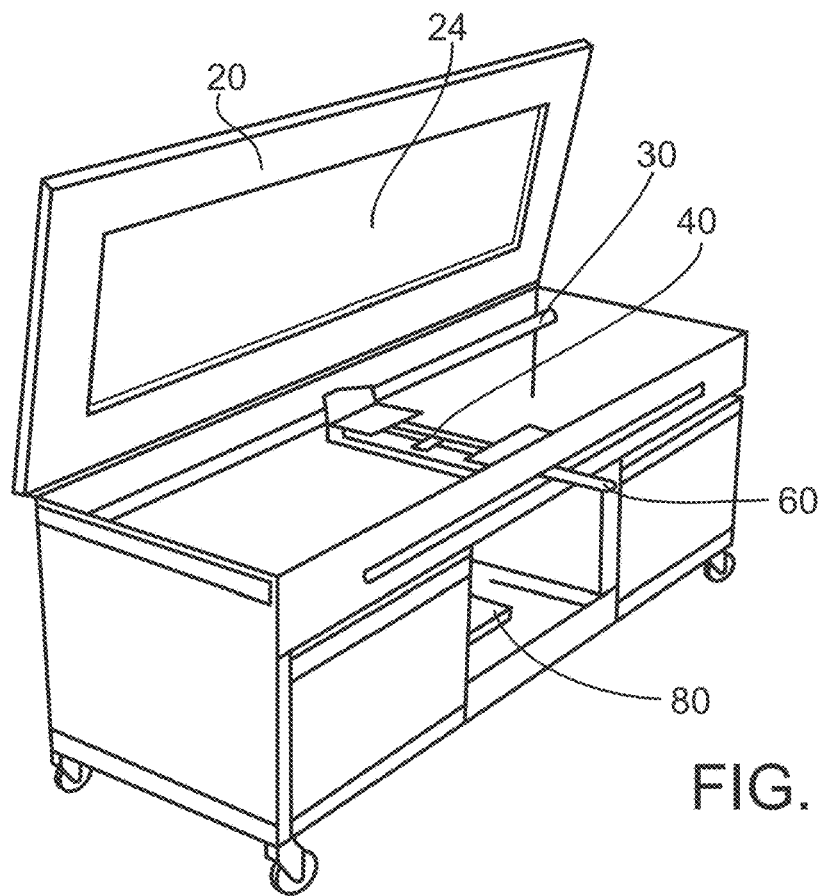
FIG. 3 is a side proximal view of one embodiment of a table used in the instant invention.
Figure 4:
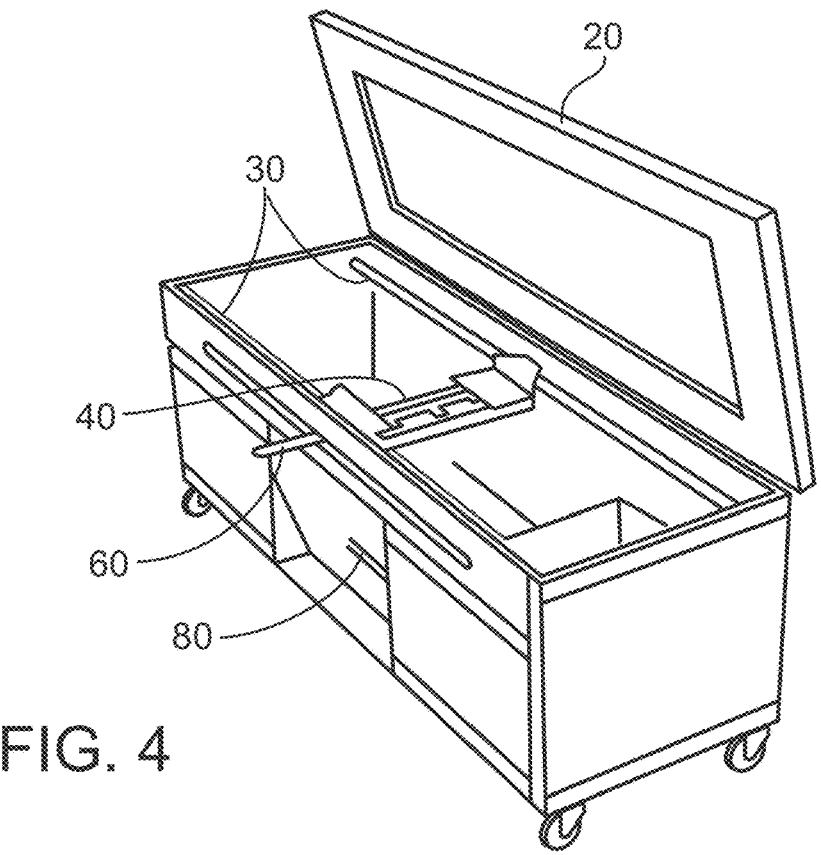
FIG. 4 is a side proximal view of one embodiment of a table used in the instant invention.
Figure 5:
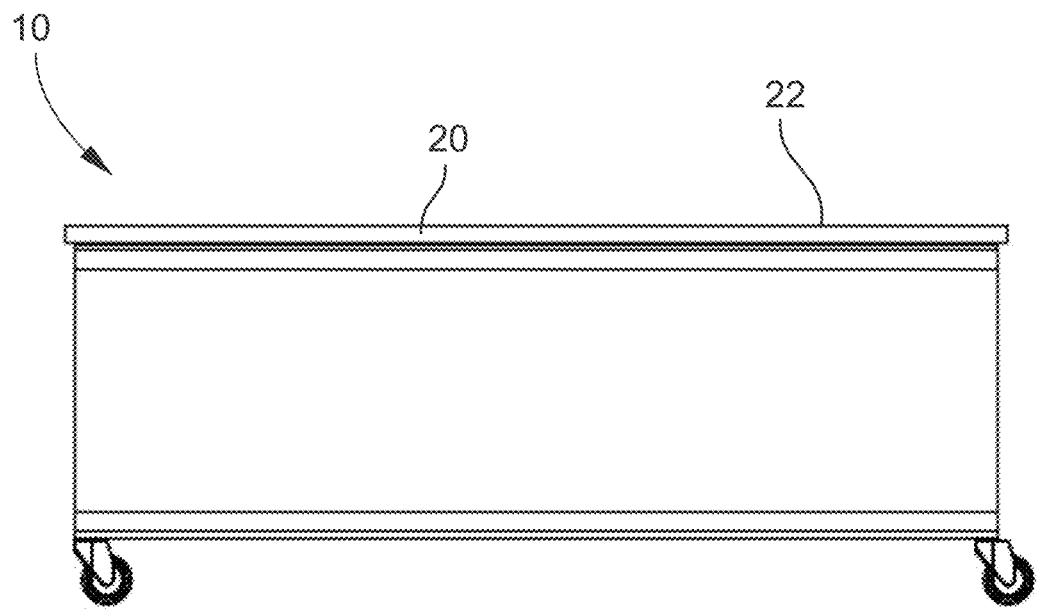
FIG. 5 is a rear view of one embodiment of a table used in the instant invention.
Figure 6:
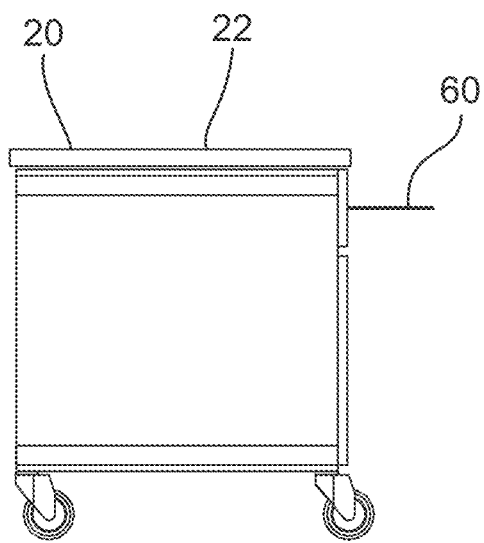
FIG. 6 is a side view of one embodiment of a table used in the instant invention.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The instant invention is an apparatus 10 used to treat patients, both human and animal, for a variety of ailments. Treatments include, but are not limited to, relaxation of muscle spasms, prevention of atrophy resulting from disuse, increasing blood circulation, muscle re-education, post-surgical muscle stimulation, venous thrombosis prevention, and maintenance and/or increasing range of motion. The treatments are carried out using a non-invasive magnetic induction system called Extracorporeal Magnetic Innervation (ExMI). The apparatus 10 can stimulate tissue up to 10 cm in depth with no skin contact required. In use, the hertz (Hz) effects the pulse rate (contraction) and the amount of power effects the depth. Once engaged, the magnetic pulse depolarized the potassium and sodium ions within the cell wall. The causes the muscle to contract at a rate set by the system. The contraction is completely involuntary and has been proven to create new neuropathways between the brain and the muscle group.

TABLE 1

REACT Therapy Physics

| | |
|---|---|
| Depth: 4 inches to 3.5 inches (Depth) | Depth: 2 inches (Mid-Range) |
| Deep Tissue Manipulation | Deep Tissue Manipulation & Pain |
| Disuse Atrophy | Used primarily in prone position |
| 2 is used for warmup and patient introduction | for Psoas |
| | Also effective in AC joint/shoulder |
| Commonly used in most protocols | 23 Hz |
| 2 Hz & 10 Hz | |
| Depth: 1.25 inches (Mid-Range) | Depth: .75-1 inches (Shallow) |
| Pain Management and ROM | Pain Management and ROM |
| Used throughout body | Used throughout body |
| Commonly used in most protocols | Peripheral nerves, often used in lower back and during spasm |
| 34 Hz | 50 Hz |

The use of the apparatus is most simply completed in three steps.
1. The patient lies on the platform and the magnetic nerve/muscle stimulator is adjusted and positioned beneath the desired muscle region.
2. The power and Hz are adjusted to the desired levels
3. The muscle group is treated for the desired length of time.

The instant invention includes an apparatus 10 for muscle stimulation comprising a platform 20 with an upper surface 22 and a lower surface 24, a pair of cross rails 30 are mounted under the lower surface 24 of the table 20 and a sled 40 slidably mounted to the cross rails 30. The platform 20 can be a table 91 or a bed 92. A pair of sled rails 45 are mounted to the sled 40 and a bracket 50 is slidably mounted to the sled rails 45. A handle 60 secured to the bracket 50 and the handle 60 allows an operator or machine to adjust the location of the bracket 50 to any location desired under the platform 20. A magnetic nerve/muscle stimulator 70 is mounted to the bracket 50 which includes one or more magnets 72 and one or more electrical coils 74, and a control panel 80 is operationally associated with the magnetic nerve/muscle stimulator 70. A control panel 80 controls the power supplied and the frequency (Hz) of the magnetic nerve/muscle stimulator 70 which generates and directs a magnetic field into the anatomy of a patient positioned on the upper surface of the platform 22.

The instant invention also includes an apparatus 10 for muscle stimulation comprising a platform 20 with an upper surface 22 and a lower surface 24, one or more pairs of cross rails 30 mounted under the lower surface 24 of the platform 20 and one or more sleds 40 slidably mounted to each pair of cross rails 30. The platform 20 can be a table 91 or a bed 92. A pair of sled rails 45 are mounted to each sled and a bracket 50 is slidably mounted to each pair of sled rails 45. A magnetic nerve/muscle stimulator 70 is mounted to each bracket 50 which includes one or more magnets 72 and one or more electrical coils 74 where the magnetic nerve/muscle stimulator 70 generates and directs a magnetic field into the anatomy of a patient positioned on the upper surface 22 of the platform 20. One or more actuators operationally associated with each bracket 50 where the actuators move each bracket 50 along the x-axis and y-axis beneath the platform along the cross rails 30 and sled rails 45. A control panel 80 is operationally associated with the magnetic nerve/muscle stimulator 70, the control panel 80 controlling the power supplied to the magnetic nerve/muscle stimulator 70. A CPU/processing computer 90 is operationally associated with the control panel 80 and the actuators and one or more processors, a computer readable memory, and a computer readable storage medium operatively associated with the CPU/processing computer. A treatment module which includes programming instructions to execute one or more treatment programs, directing each bracket 50 to specific coordinates beneath the platform 20 and supplying each coil 74 with an amount of power for a duration at a frequency.

The instant invention also includes an apparatus 10 for muscle stimulation comprising a chair 94 including a seat 95 with an upper surface and a lower surface, a back 96 engaged to the seat 95, the back 96 having an upper surface and a lower surface, one or more arm supports 97 engaged to the seat 95, the arm supports 97 having an upper surface and a lower surface, and one or more leg supports 98 engaged to the seat 95, the leg supports 98 having an upper surface and a lower surface. One or more pairs of cross rails 30 are mounted under the lower surface of the seat 95, back 96, arm supports 97, and/or leg supports 98 with one or more sleds 40 slidably mounted to each pair of cross rails 30. A pair of sled rails 45 are mounted to each sled 40 and a bracket 50 is slidably mounted to each pair of sled rails 45. A magnetic nerve/muscle stimulator 70 is mounted to each bracket 50 which includes one or more magnets 72 and one or more electrical coils 74 where each magnetic nerve/muscle stimulator 70 generates and directs a magnetic field into the anatomy of a patient positioned on the upper surface of the seat 95, back 96, arm supports 97, and/or leg supports 98. One or more actuators are operationally associated with each bracket 50 where the actuators move each bracket 50 along the x-axis and y-axis beneath the surfaces of the chair along the cross rails 30 and sled rails 45. A control panel 80 is operationally associated with the magnetic nerve/muscle stimulator 70, the control panel 80 controlling the power supplied to the magnetic nerve/muscle stimulator 70. A CPU/processing computer 90 is operationally associated with the control panel 80 and the actuators and one or more processors, a computer readable memory, and a computer readable storage medium operatively associated with the CPU/processing computer and a treatment module which includes programming instructions to execute one or more treatment programs, directing each bracket to specific coordinates beneath the chair elements and supplying each coil with an amount of power for a duration at a frequency.

The above apparatus 10 can further include one or more foot supports 99 engaged to the leg supports 98 or the chair 94. One or more pairs of cross rails 30 are mounted under the lower surface of the foot supports 99 with one or more sleds 40 slidably mounted to each pair of cross rails 30. A pair of sled rails 45 are mounted to each sled 40 and a bracket 50 is slidably mounted to each pair of sled rails 45. A magnetic nerve/muscle stimulator 70 is mounted to each bracket 50 which includes one or more magnets 72 and one or more electrical coils 74 where each magnetic nerve/muscle stimulator 70 generates and directs a magnetic field into the anatomy of a patient positioned on the upper surface of the foot supports 99. One or more actuators are operationally associated with each bracket 50 where the actuators move each bracket 50 along the x-axis and y-axis beneath the surfaces of the chair along the cross rails 30 and sled rails 45. A control panel 80 is operationally associated with the magnetic nerve/muscle stimulator 70, the control panel 80 controlling the power supplied to the magnetic nerve/muscle stimulator 70. A CPU/processing computer 90 is operationally associated with the control panel 80 and the actuators and one or more processors, a computer readable memory, and a computer readable storage medium operatively associated with the CPU/processing computer and a treatment module which includes programming instructions to execute one or more treatment programs, directing each bracket to specific coordinates beneath the chair elements and supplying each coil with an amount of power for a duration at a frequency.

The apparatus 10 for muscle stimulation can include a treatment module that includes programs with programming instructions which are selected for each individual patient based on factors such as selected treatment, prognosis, age, fitness level, treatment goals, physical limitations, and physiological limitations. The treatment module also includes treatment programs which operate multiple magnetic nerve/muscle stimulators simultaneously to generate cross patters of magnetic fields within a patient.

Figure 7:
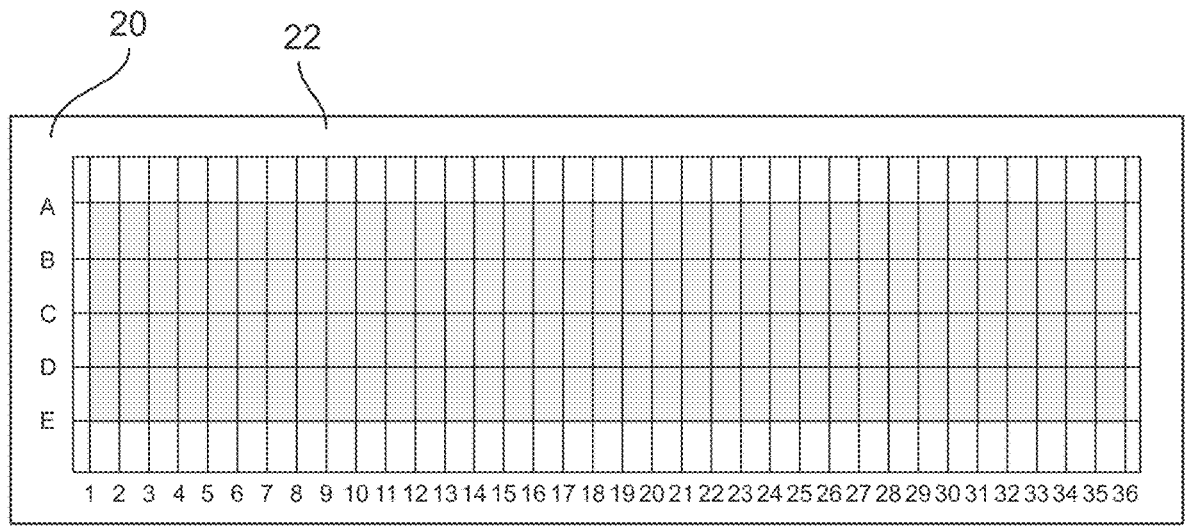
FIG. 7 is a view of one embodiment of the grid used on a table in the instant invention.
Figure 8:
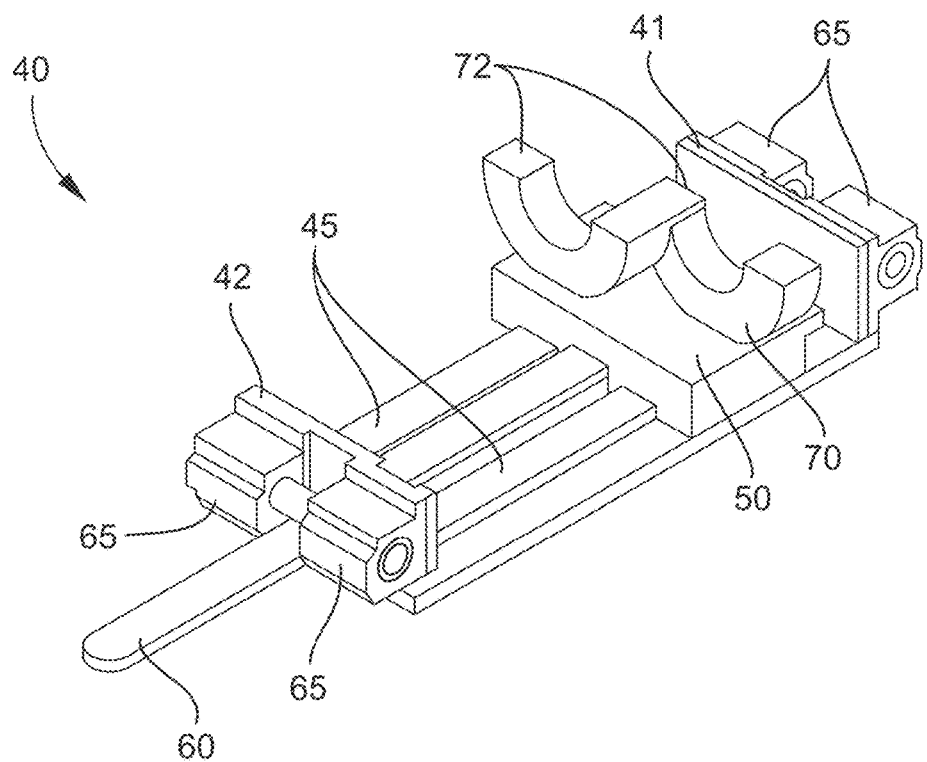
FIG. 8 is a proximal view of one embodiment of a sled used in the instant invention.
Figure 9:
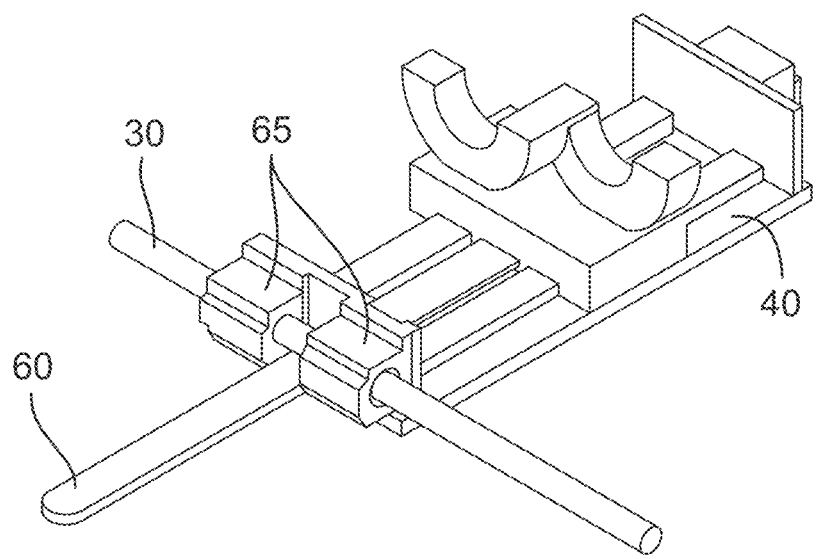
FIG. 9 is a proximal view of one embodiment of a sled used in the instant invention.
Figure 10:
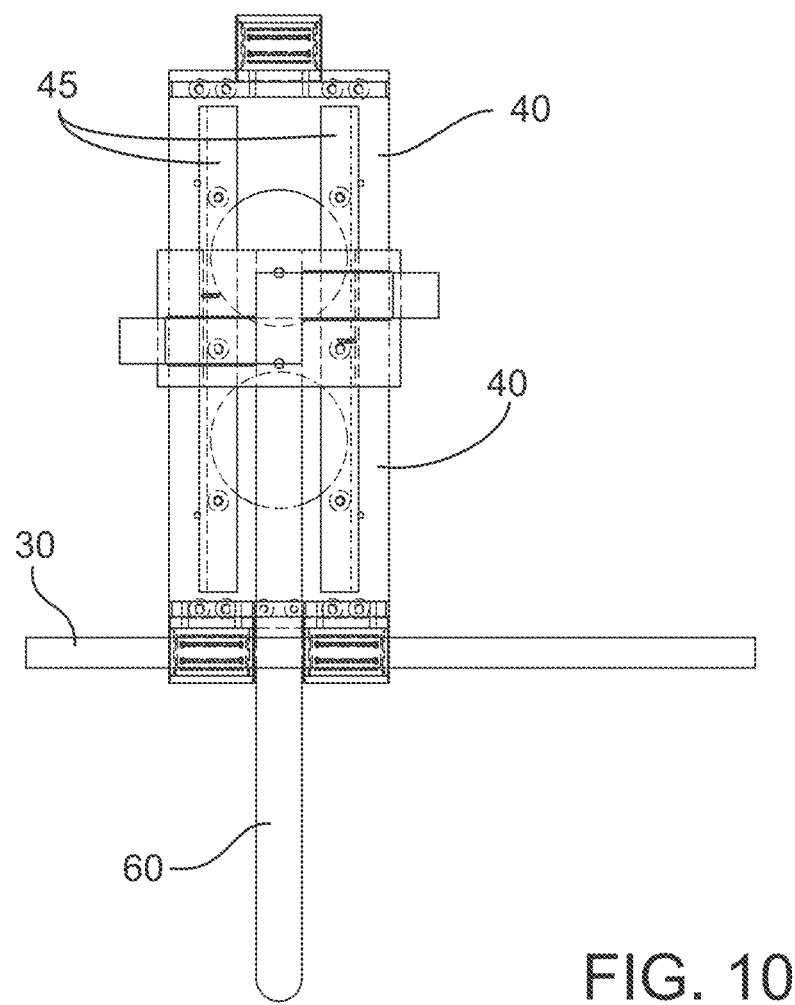
FIG. 10 is a downward view of one embodiment of a sled used in the instant invention.
Figure 11:
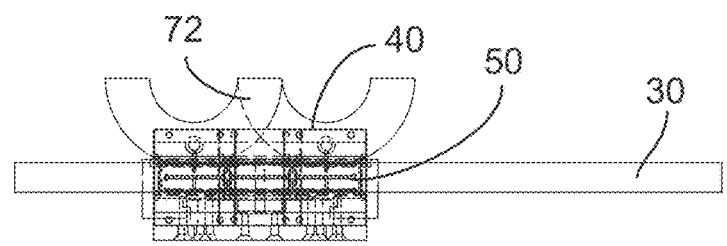
FIG. 11 is a front view of one embodiment of a sled used in the instant invention.
Figure 12:
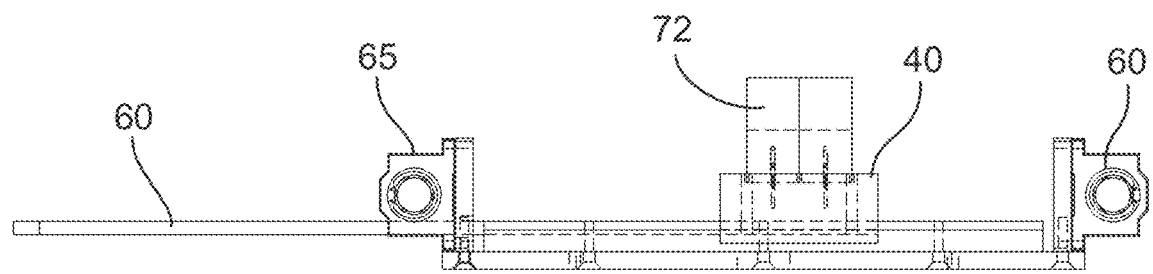
FIG. 12 is a side view of one embodiment of a sled used in the instant invention.
Figure 13:
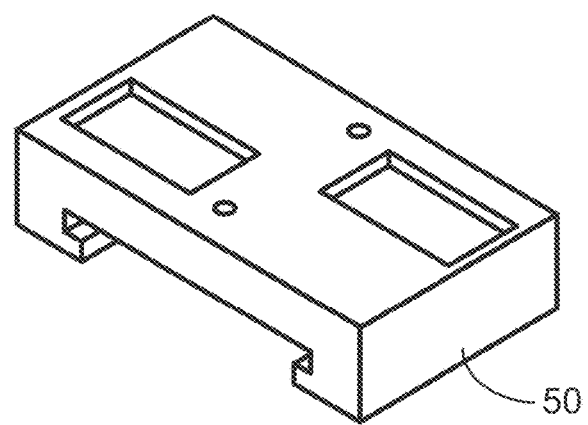
FIG. 13 is a proximal view of one embodiment of a bracket used in the instant invention.
Figure 14:
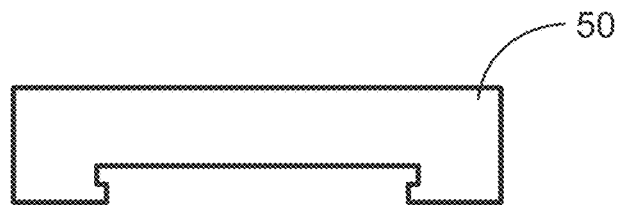
FIG. 14 is a front view of one embodiment of a bracket used in the instant invention.
Figure 15:
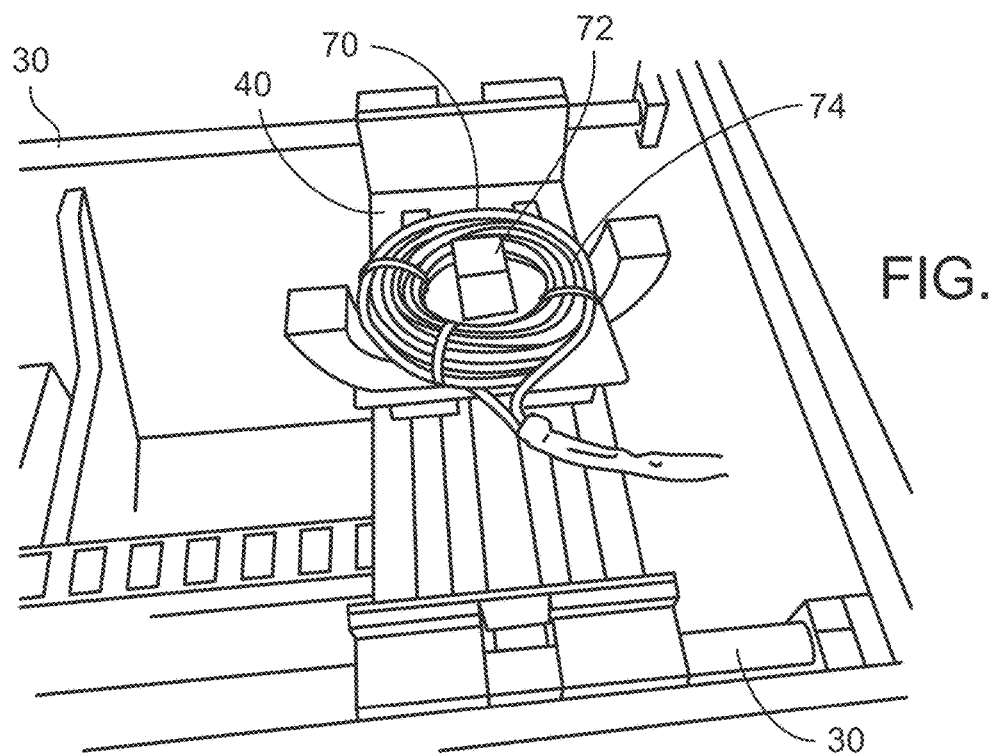
FIG. 15 is a proximal view of one embodiment of a magnetic nerve/muscle stimulator used in the instant invention.

The apparatus 10 for muscle stimulation can also include a letter diagram located on the handle 60 which corresponds to a location on the y-axis for the bracket 50 and a number diagram located on the platform 20 which corresponds to a location on the x-axis for the bracket 50. One embodiment of this is shown in FIGS. 17 and 18. The apparatus 10 can also include a grid diagram printed on the upper surface of the platform 22 (FIG. 7), where the grid diagram shows the corresponding letter diagram and number diagram locations allowing an operator to position the bracket 50 in an area under the platform to direct the magnetic field into the anatomy of a patient positioned on the upper surface of the platform 22. The grid diagram also allows an operator to correctly position a patient on the platform 20 to ensure the proper muscle groups are treated.

Figure 16:
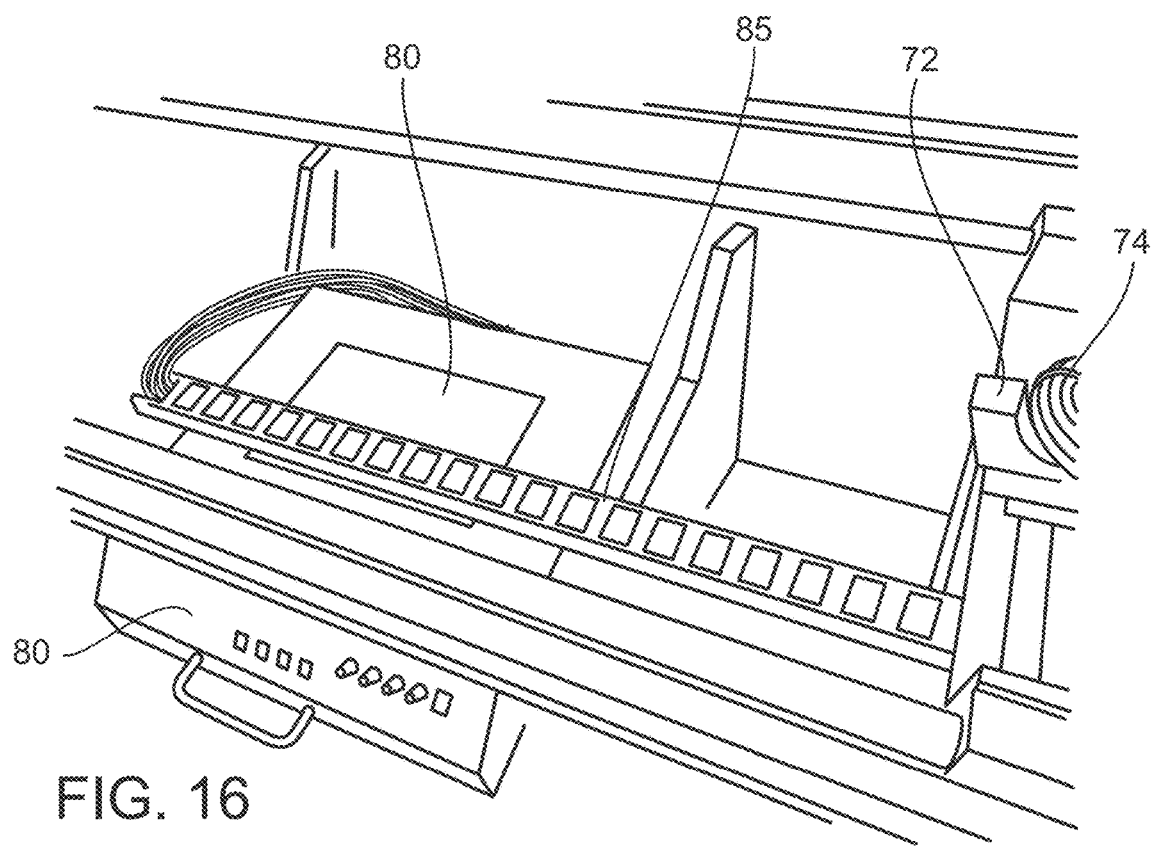
FIG. 16 is a proximal view of one embodiment of a cord cradle used in the instant invention.
Figure 19:
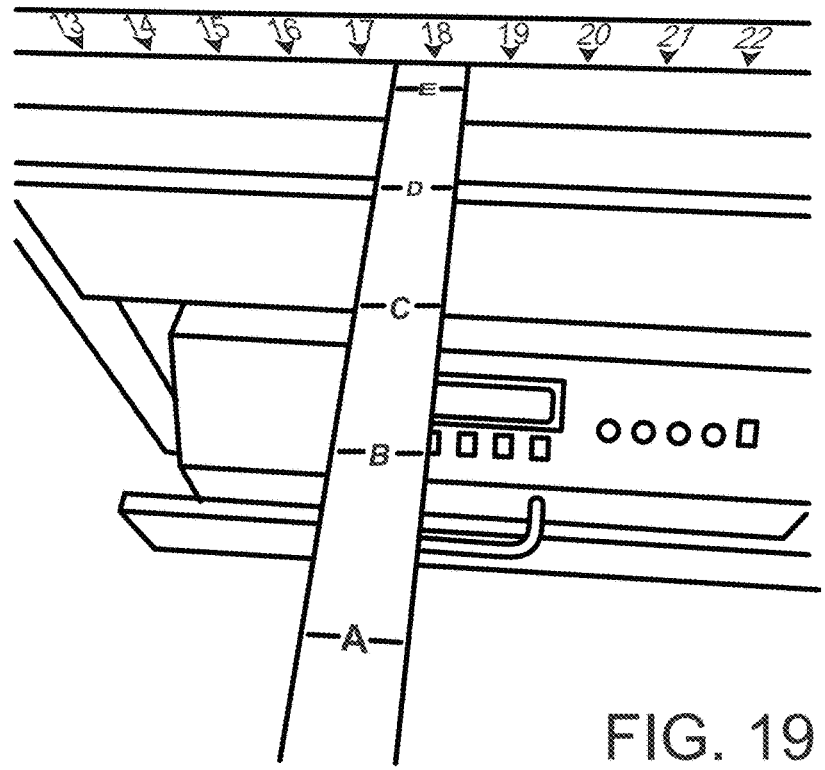
FIG. 19 is an embodiment of a letter diagram on the handle and a number diagram on the table of the instant invention.
Figure 20:
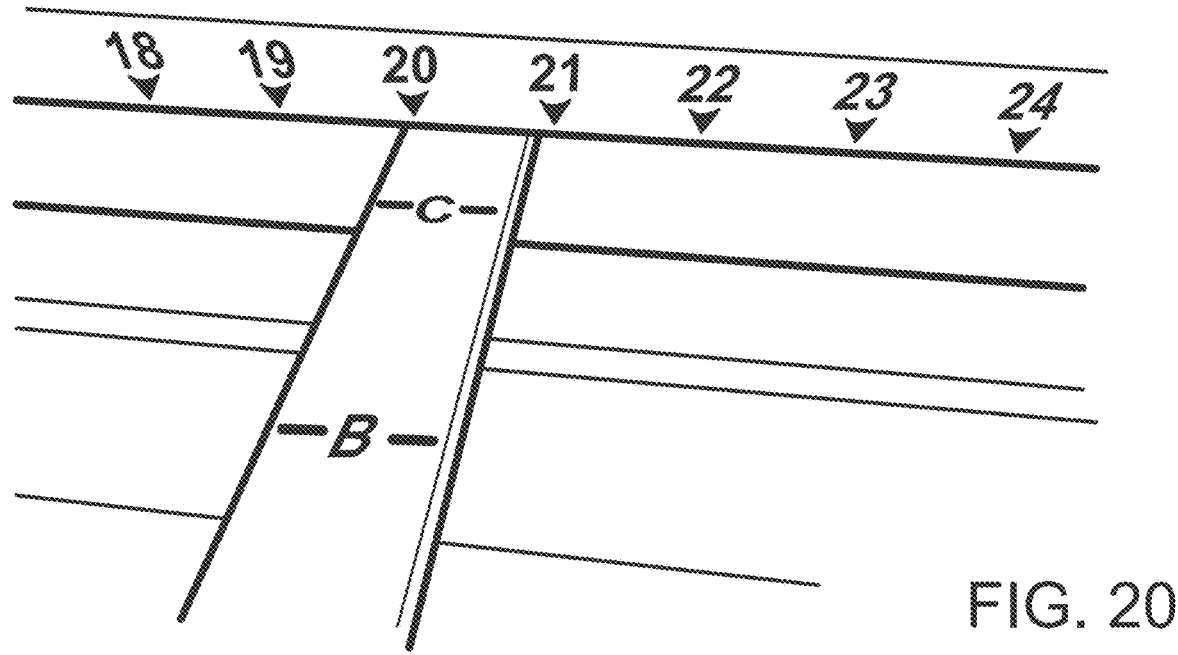
FIG. 20 is an embodiment of a letter diagram on the handle and a number diagram on the table of the instant invention.
Figure 21:
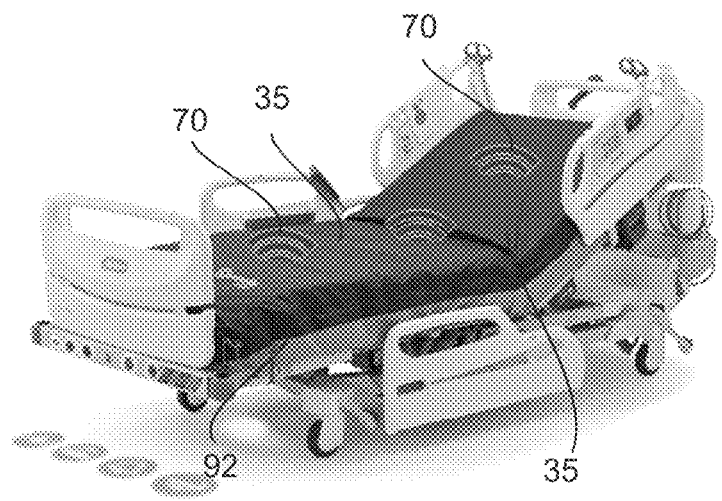
FIG. 21 is proximal view of one embodiment of a bed used in the instant invention.
Figure 22:
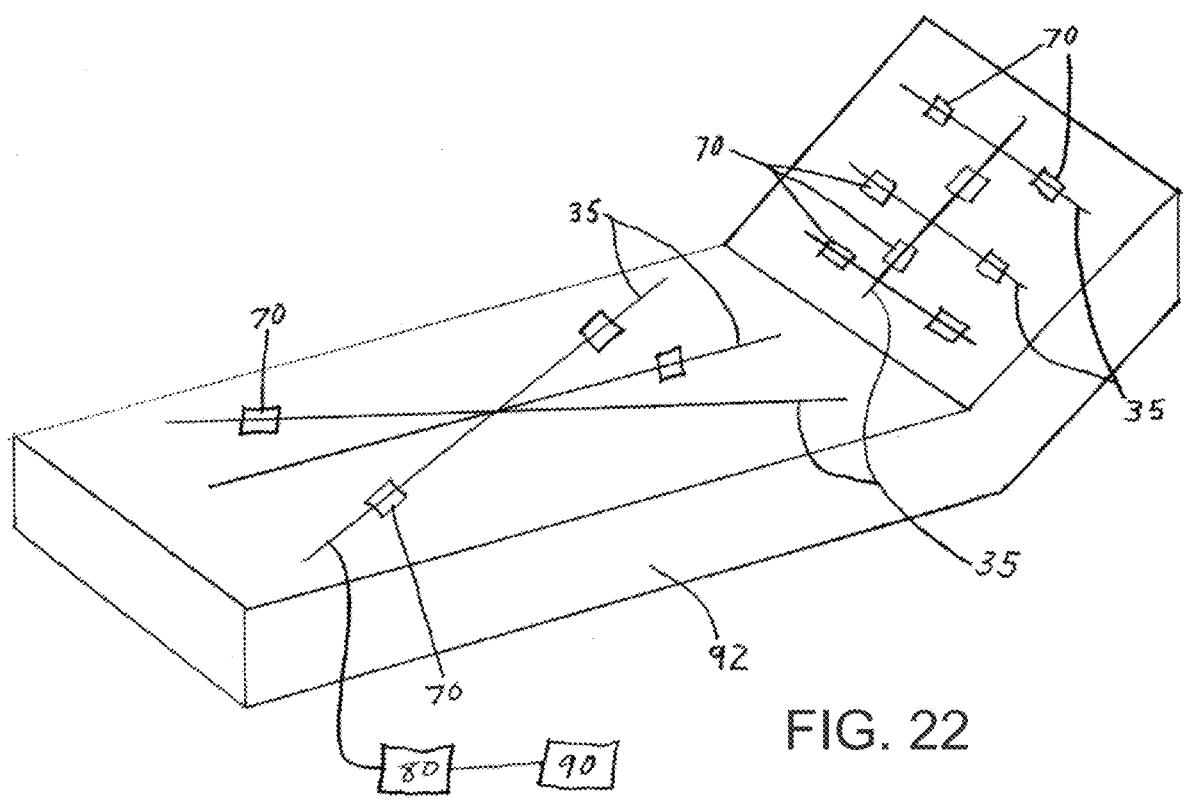
FIG. 22 is proximal view of one embodiment of a bed used in the instant invention.
Figure 23:
FIG. 23 is proximal view of one embodiment of a chair used in the instant invention.
Figure 24:
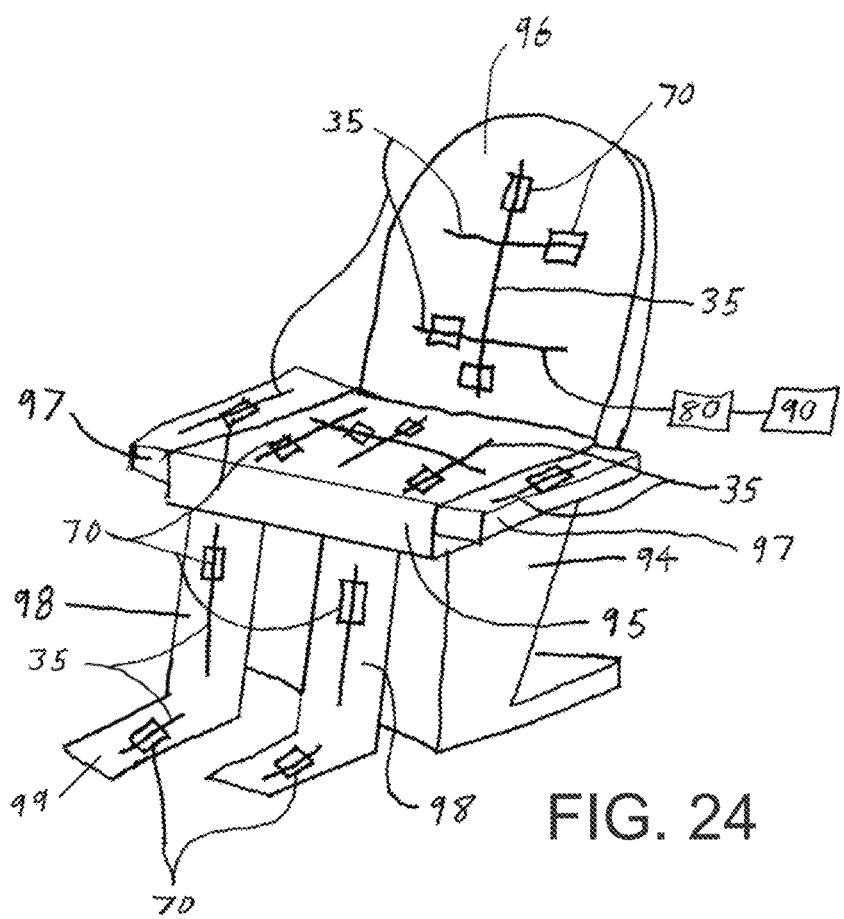
FIG. 24 is proximal view of one embodiment of a chair used in the instant invention.
Figure 25:
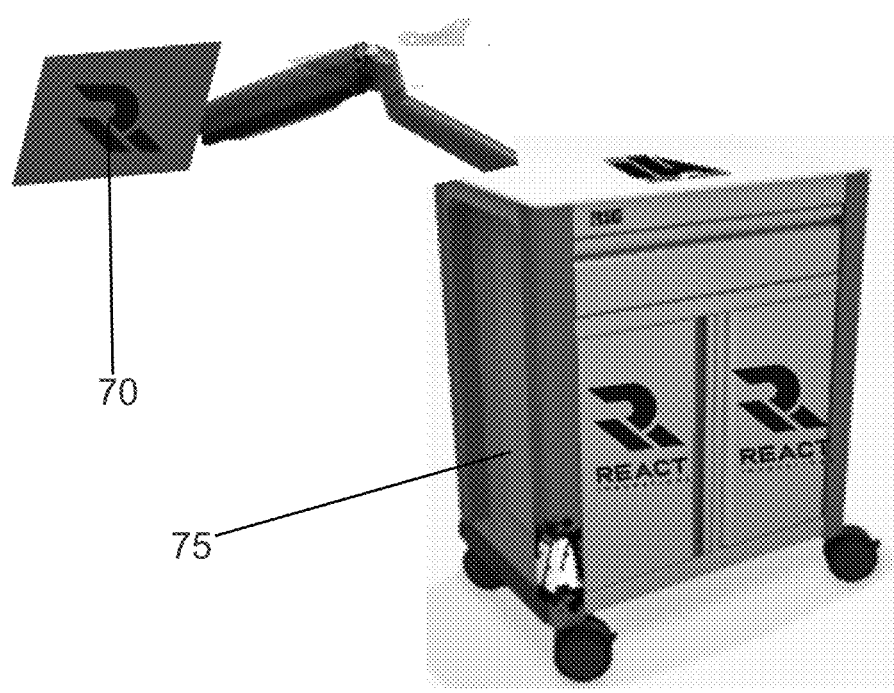
FIG. 25 is proximal view of one embodiment of a mobile cart used in the instant invention.

The apparatus 10 can also include a cord cradle 85 (FIG. 16), wherein wires for the electrical coils are routed through the cord cradle 85 to manage and protect the wires while the bracket 50 is moved. The magnetic nerve/muscle stimulator 70 within the apparatus 10 is adapted to stimulate nerves which cause contraction of muscles located within the generated magnetic field.

The lower surface of the platform 24 can be recessed, and the magnetic nerve/muscle stimulator 70 is located within the recessed area. This decreases the thickness of the platform 20, allowing the magnetic nerve/muscle stimulator 70 to be located closer to the patient. The thickness of the platform 20 is in the range of 0.1 to 3.0 cm, 0.2 to 3.0 cm, 0.3 to 3.0 cm, 0.4 to 3.0 cm, 0.5 to 3.0 cm, 0.6 to 3.0 cm, 0.7 to 3.0 cm, 0.8 to 3.0 cm, 0.9 to 3.0 cm, 1.0 to 3.0 cm, 1.5 to 3.0 cm, 2.0 to 3.0 cm, or any combination thereof.

The apparatus 10 for muscle stimulation can also include one or more actuators operationally associated with the bracket 50 where the actuators move the bracket 50 along the x-axis and y-axis, locating the magnetic nerve/muscle stimulator 70 in any location desired beneath the platform 20. A CPU/processing computer is operationally associated with the control panel 80 and the actuators and electronic storage is operationally associated with the CPU/processing computer. The CPU/processing computer is capable of executing one or more programs stored on the electronic storage, supplying the coils with a specific amount of power and adjusting the wavelength generated, directing the bracket 50 to specific coordinates on the platform 20 for a specific duration.

The apparatus 10 for muscle stimulation can also include an optical scanner or pressure pad operationally associated with the control panel 80 and the CPU/processing computer 90 which are capable of detecting a patient and a sensor module which includes programming instructions to detect the location of the patient's torso, head, arms and legs and relay sensor data to the CPU/processing computer 90 where the sensor data is used by the treatment module to direct the one or more magnetic nerve/muscle stimulators 70 to carry out one or more treatment programs.

The instant invention also includes a portable version of the apparatus 10 for muscle stimulation as described above. The mobile unit 75 can include one magnetic nerve/muscle stimulator 70 which is located under the surface of a platform 20 and also include another magnetic nerve/muscle stimulator 70 secured to a manipulatable arm, allowing a user to locate the magnetic nerve/muscle stimulator 70 in any desired location on a patient. The portable version can also include a single magnetic nerve/muscle stimulator 70 secured to a manipulatable arm. The portable version may also be a seat/stool design with a fixed magnetic nerve/muscle stimulator 70 located under the seat.

The instant invention allows a single operator can control two or more apparatuses 10 from a single CPU/processing computer 90. A CPU/processing computer can include any kind of computer known in the art including, but not limited to, desktops, laptops, tablets, smart devices, smart phones, or any combination thereof. The instant invention can also be controlled remotely using any device or technology known in the art including, but not limited to, through the internet (wired or wireless), Bluetooth, radio frequency, or any combination thereof.

The instant invention also includes a method for stimulating specific muscles and/or muscle groups comprising the steps of:
a. providing an apparatus 10 for muscle stimulation comprising a table 20 with an upper surface 22 and a lower surface 24, a pair of cross rails 30 are mounted under the lower surface 24 of the table 20 and a sled 40 slidably mounted to the cross rails 30. A pair of sled rails 45 are mounted to the sled 40 and a bracket 50 is slidably mounted to the sled rails 45. A handle 60 secured to the bracket 50 and the handle 60 allows an operator or machine to adjust the location of the bracket 50 to any location desired under the table 20. A magnetic nerve/muscle stimulator 70 is mounted to the bracket 50 which includes one or more magnets 72 and one or more electrical coils 74, and a control panel 80 is operationally associated with the magnetic nerve/muscle stimulator 70. A letter diagram is located on the handle 60 which corresponds to a location on the y-axis for the bracket 50 and a number diagram located on the table 20 which corresponds to a location on the x-axis for the bracket 50;
b. positioning a patient on the upper surface 22 of the table 20;
c. moving and locating the bracket 50 into a desired position under the table 20 and the patient;
d. activating the control panel 80 to supply power to the magnetic nerve/muscle stimulator 70 and generate a magnetic field with the magnetic nerve/muscle stimulator 70;
e. directing the magnetic field into the anatomy of the patient positioned on the upper surface 22 of the table 20 for a desired length of time; and
f. repeating steps (c), (d) and (e) until the patient's treatment is complete.

The instant invention also includes a method for stimulating specific muscles and/or muscle groups comprising the steps of:
a. providing an apparatus 10 for muscle stimulation comprising a platform 20 with an upper surface 22 and a lower surface 24, one or more pairs of cross rails 30 mounted under the lower surface 24 of the platform 20, one or more sleds 40 slidably mounted to each pair of cross rails 30, a pair of sled rails 45 mounted to each sled 40, a bracket 50 slidably mounted to each pair of sled rails 45 and a magnetic nerve/muscle stimulator 70 mounted to each bracket 50 which includes one or more magnets 72 and one or more electrical coils 74, where the magnetic nerve/muscle stimulator 70 generates and directs a magnetic field into the anatomy of a patient positioned on the upper surface of the platform. One or more actuators are operationally associated with the bracket 50 where the actuators move each bracket 50 along the x-axis and y-axis beneath the platform along the cross rails 30 and sled rails. A control panel 80 is operationally associated with the magnetic nerve/muscle stimulator 70, the control panel 80 controlling the power supplied to the magnetic nerve/muscle stimulator 70. A CPU/processing computer 90 is operationally associated with the control panel 80 and the actuators and one or more processors, a computer readable memory, and a computer readable storage medium are operatively associated with the CPU/processing computer. A treatment module which includes programming instructions to execute one or more treatment programs, directing each bracket 50 to specific coordinates beneath the platform 20 and supplying each coil 72 with an amount of power for a duration at a frequency;
b. positioning a patient on the upper surface 22 of the platform 20;
c. moving and locating each bracket 50 into a desired position under the platform 20 and the patient using the CPU/processing computer;
d. engaging the treatment module and selecting one or more treatment programs to treat the patient;
e. executing the one or more treatment programs to engage the control panel to supply power to the magnetic nerve/muscle stimulator and generate a magnetic field with the magnetic nerve/muscle stimulator;
f. directing the magnetic field into the anatomy of the patient positioned on the upper surface of the platform 20 for a desired length of time; and
g. repeating steps (c), (d), (e) and (f) until the patient's treatment is complete.

The above methods may further include a grid diagram printed on the upper surface 22 of the table 20, the grid diagram showing the corresponding letter diagram and number diagram locations allowing an operator to position the bracket 50 in an area under the table 20 to direct the magnetic field into the anatomy of a patient positioned on the upper surface 22 of the table 20. The method as described where the magnetic nerve/muscle stimulator 70 is adapted to stimulate nerves which cause contraction of muscles located within the generated magnetic field.

The above methods may further include one or more actuators operationally associated with each bracket 50 where the actuators move the bracket 50 along the x-axis and y-axis, locating the magnetic nerve/muscle stimulator 70 in any location desired beneath the table. A CPU/processing computer is operationally associated with the control panel 80 and the actuators and electronic storage is operationally associated with the CPU/processing computer. The CPU/processing computer is capable of executing one or more programs stored on the electronic storage, supplying the coils with a specific amount of power and adjusting the wavelength generated, directing the bracket 50 to specific coordinates on the table for a specific duration.

The above methods can further include an optical scanner or pressure pad operationally associated with the control panel 80 and the CPU/processing computer 90 which are capable of detecting a patient and a sensor module which includes programming instructions to detect the location of the patient's torso, head, arms and legs and relay sensor data to the CPU/processing computer 90 where the sensor data is used by the treatment module to direct the one or more magnetic nerve/muscle stimulators 70 to carry out one or more treatment programs.

The treatment module includes treatment programs which operate multiple magnetic nerve/muscle stimulators simultaneously to generate cross patters of magnetic fields within a patient.

Any method described herein may incorporate any design element contained within this application and any other document/application incorporated by reference herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The present invention may be embodied in other forms without departing from the spirit and the essential attributes thereof, and, accordingly, reference should be made to the appended claims, rather than to the foregoing specification, as indicating the scope of the invention. The invention illustratively disclosed herein suitably may be practiced in the absence of any element which is not specifically disclosed herein.

The invention claimed is:

1. An apparatus for muscle stimulation comprising:
    a platform with an upper surface and a lower surface;
    a pair of cross rails mounted under the lower surface of the platform;
    a sled slidably mounted to each cross rail of the pair of cross rails;
    a pair of sled rails, wherein each sled rail is mounted to each the sled;
    a bracket slidably mounted to each sled rail of the pair of sled rails;
    a magnetic nerve/muscle stimulator mounted to the bracket which includes one or more magnets and one or more electrical coils;
        wherein the magnetic nerve/muscle stimulator is configured to generate and direct a magnetic field to a patient positioned on the upper surface of the platform;
    one or more actuators operationally associated with the bracket;
        wherein the one or more actuators move the bracket along an x-axis and y-axis beneath the platform along the cross rails and sled rails;
    a control panel operationally associated with the magnetic nerve/muscle stimulator, wherein the control panel controls power supplied to the magnetic nerve/muscle stimulator;
    a CPU/processing computer operationally associated with the control panel and the one or more actuators;
    one or more processors, a computer readable memory, and a computer readable storage medium operatively associated with the CPU/processing computer; and
    a treatment module which includes programming instructions to execute one or more treatment programs, directing the bracket to specific coordinates beneath the platform and supplying each of the one or more electrical coils with an amount of power for a duration at a frequency;
        wherein the one or more treatment programs include programming instructions which are selected for the patient based on factors comprising: selected treatment, prognosis, age, fitness level, treatment goals, physical limitations, and physiological limitations.

2. The apparatus for muscle stimulation of claim 1 further including one or more cord cradles, wherein wires for the one or more electrical coils are routed through the one or more cord cradles to manage and protect the wires while the bracket is moved.

3. The apparatus for muscle stimulation of claim 1 wherein the lower surface of the platform is recessed, forming a recessed area, and the magnetic nerve/muscle stimulator is located within the recessed area.

4. The apparatus for muscle stimulation of claim 1 further comprising:
    an optical scanner or pressure pad operationally associated with the control panel and the CPU/processing computer which are capable of detecting the patient; and
    a sensor module which includes programming instructions to detect a location of a patient's torso, head, arms and legs and generate and relay sensor data to the CPU/processing computer;
        wherein the sensor data is used by the treatment module to direct the magnetic nerve/muscle stimulator to carry out the one or more treatment programs.

5. The apparatus for muscle stimulation of claim 1 wherein the treatment module includes the one or more treatment programs, which operate the magnetic nerve/muscle stimulator and additional magnetic nerve/muscle stimulators installed within the apparatus simultaneously to generate cross patterns of magnetic fields within the patient.

6. A system for muscle stimulation including the apparatus of claim 1 wherein a single operator can control two or more apparatuses from the CPU/processing computer.

7. A method for stimulating specific muscles and/or muscle groups to facilitate treatment of a patient comprising the steps of:
   a. providing an apparatus for muscle stimulation comprising:
      a platform with an upper surface and a lower surface;
      a pair of cross rails mounted under the lower surface of the platform;
      a sled slidably mounted to each cross rail of the pair of cross rails;
      a pair of sled rails, wherein each sled rail is mounted to the sled;
      a bracket slidably mounted to each sled rail of the pair of sled rails;
      a magnetic nerve/muscle stimulator mounted to the bracket which includes one or more magnets and one or more electrical coils;
         wherein the magnetic nerve/muscle stimulator is configured to generate and direct a magnetic field to a patient positioned on the upper surface of the platform;
      one or more actuators operationally associated with the bracket;
         wherein the one or more actuators move the bracket along an x-axis and y-axis beneath the platform along the cross rails and sled rails;
      a control panel operationally associated with the magnetic nerve/muscle stimulator, wherein the control panel controls an amount of power supplied to the magnetic nerve/muscle stimulator;
      a CPU/processing computer operationally associated with the control panel and the one or more actuators;
      one or more processors, a computer readable memory, and a computer readable storage medium operatively associated with the CPU/processing computer; and
      a treatment module which includes programming instructions to execute one or more treatment programs, directing the bracket to specific coordinates beneath the platform and supplying each of the one or more electrical coils with the amount of power for a duration at a frequency;
   b. positioning the patient on the upper surface of the platform;
   c. moving and locating the bracket into a desired position under the platform and the patient using the CPU/processing computer;
   d. engaging the treatment module and selecting the one or more treatment programs to treat the patient;
   e. executing the one or more treatment programs to engage the control panel to supply the amount of power to the magnetic nerve/muscle stimulator and generate the magnetic field with the magnetic nerve/muscle stimulator;
   f. directing the magnetic field to the patient positioned on the upper surface of the platform for a desired length of time; and
   g. repeating steps (c), (d), (e) and (f) until pain of the patient is alleviated.

8. The method of claim 7 wherein the one or more treatment programs include programming instructions which are selected for the patient based on factors comprising: selected treatment, prognosis, age, fitness level, treatment goals, physical limitations, and physiological limitations.

9. The method of claim 7 further including one or more cord cradles, wherein wires for the one or more electrical coils are routed through the one or more cord cradles to manage and protect the wires while the bracket is moved.

10. The method of claim 7 wherein the lower surface of the platform is recessed, forming a recessed area, and the magnetic nerve/muscle stimulator is located within the recessed area.

11. The method of claim 7 further comprising:
   an optical scanner or pressure pad operationally associated with the control panel and the CPU/processing computer which are capable of detecting the patient; and
   a sensor module which includes programming instructions to detect a location of a patient's torso, head, arms and legs and generate and relay sensor data to the CPU/processing computer;
      wherein the sensor data is used by the treatment module to direct the magnetic nerve/muscle stimulator to carry out the one or more treatment programs.

12. The method of claim 7 wherein the treatment module includes the one or more treatment programs, which operate the magnetic nerve/muscle stimulator and additional magnetic nerve/muscle stimulators installed within the apparatus simultaneously to generate cross patterns of magnetic fields within the patient.

13. The method of claim 7 wherein a single operator can control two or more apparatuses for muscle stimulation from the CPU/processing computer.

* * * * *